United States Patent [19]

Chou

[11] Patent Number: 5,456,839
[45] Date of Patent: Oct. 10, 1995

[54] METHOD OF DEHYDRATING ORGANIC OXYGENATES

[75] Inventor: Kechia J. Chou, Wappingers Falls, N.Y.

[73] Assignee: Texaco Inc., White Plains, N.Y.

[21] Appl. No.: 733,516

[22] Filed: Jul. 22, 1991

[51] Int. Cl.$^6$ .................................................. B01D 61/36
[52] U.S. Cl. ...................... 210/638; 210/640; 210/500.37
[58] Field of Search .................................. 210/640, 654, 210/500.37, 638

[56] References Cited

U.S. PATENT DOCUMENTS

| | | | |
|---|---|---|---|
| 3,723,306 | 3/1973 | Bridgeford | 210/644 |
| 3,927,242 | 12/1975 | Rembaum et al. | 428/411 |
| 4,035,291 | 7/1977 | Chiang et al. | 210/640 |
| 4,865,743 | 9/1989 | Ellinghurst et al. | 210/640 |
| 4,992,176 | 2/1991 | Bartels | 210/500.37 X |

*Primary Examiner*—Frank Spear

[57] ABSTRACT

Aqueous solutions of organic oxygenates, such as ethylene glycol may be dehydrated by pervaporation through a poly(vinyl pyridine) membrane which has been quaternized and cross-linked.

15 Claims, No Drawings

METHOD OF DEHYDRATING ORGANIC OXYGENATES

RELATED APPLICATION

Application Ser. No. 07/425,156, filed Oct. 23, 1989 by Texaco Inc. as assignee of Craig R. Bartels, now U.S. Pat. No. 4,992,176 issued Feb. 12, 1991, the contents of which application are incorporated herein by reference.

Application Ser. No. 07/437,430, filed Nov. 16, 1989 by Texaco Inc. as assignee of Craig R. Bartels, now U.S. Pat. No. 5,152,898, the contents of which application are incorporated herein by reference.

Application Ser. No. 07/563,018, filed Aug. 6, 1990 by Texaco Inc. as assignee of Craig R. Bartels, the contents of which application are incorporated herein by reference.

Application Ser. No. 07/597,966, filed Oct. 11, 1990 by Texaco Inc. as assignee of Craig R. Bartels, the contents of which application are incorporated herein by reference.

FIELD OF THE INVENTION

This invention relates to the dehydration of organic oxygenates such as isopropyl alcohol or ethylene glycol. More particularly it relates to a membrane technique for effecting separation of water from an aqueous mixture containing isopropyl alcohol or ethylene glycol.

BACKGROUND OF THE INVENTION

As well known to those skilled in the art, it is possible to remove water from mixtures thereof with organic liquids by various techniques including adsorption or distillation. These conventional processes, particularly distillation, are however, characterized by high capital cost. In the case of distillation for example the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs principally costs of heating and cooling—plus pumping, etc.

Furthermore the properties of the materials being separated, as is evidenced by the distillation curves, may be such that a large number of plates may be required, etc. When the material forms an azeotrope with water, additional problems may be present which for example, would require that separation be effected in a series of steps (e.g. as intwo towers) or by addition of extraneous materials to the system.

There are also comparable problems which are unique to adsorption systems.

It has been found to be possible to utilize membrane systems to separate mixtures of miscible liquids by pervaporation. In this process, the charge liquid is brought into contact with a membrane film; and one component of the charge liquid preferentially permeates the membrane. The permeate is then removed as a vapor from the downstream side of the film—typically by sweeping with a carrier gas or by reducing the pressure below the saturated vapor pressure of the permeating species.

Illustrative membranes which have been employed in prior art techniques include those set forth in the following table:

TABLE

| Separating Layer | References |
| --- | --- |
| - Nafion brand of perfluorosulfonic acid | - Cabasso and Liu J. Memb. Sci. 24, 101 (1985) |
| - Sulfonated polyethylene | - Cabasso, Korngold & Liu J. Pol. Sc: Letters, 23, 57 (1985) |
| - Fluorinated polyether or Carboxylic Acid fluorides | - U.S. Pat. No. 4,526,948 to Dupont as assignee of Resnickto |
| - Selemion AMV brand of Asahi Glass cross-linked styrene butadiene (with quaternary ammonium residues on a polyvinyl chloride backing) | - Wentzlaff Boddcker & Hattanbach J. Memb. Sci. 22,333 (1985) |
| - Cellulose triacetate | - Wentzlaff, Boddeker & Hattanback, J. Memb. Sci. 22, 333 (1985) |
| - Polyacrylonitrile | - Neel, Aptel & Clement Desalination 53, 297 (1985) |
| - Crosslinked Polyvinyl Alcohol | - Eur. Patent 0 096 339 to GFT as assignee of Bruschke |
| - Poly(maleimide-acrylonitrile) | - Yoshikawa et al J. Pol. Sci. 22, 2159 (1984) |
| - Dextrine - isophorone diisocyanate | - Chem. Econ. Eng. Rev., 17, 34 (1985) |

The cost effectiveness of a membrane is determined by the selectivity and productivity. Of the membranes commercially available, an illustrative polyvinyl alcohol membrane of high performance is that disclosed in European patent 0 096 339 A2 of GFT as assignee of Bruschke—published 21 Dec. 1983.

European Patent 0 096 339 A2 to GFT as assignee of Bruschke discloses, as cross-linking agents, diacids (typified by maleic acid or fumaric acid); dihalogen compounds (typified by dichloroacetone or 1,3-dichloroisopropanol); aldehydes, including dialdehydes, typified by formaldehyde. These membranes are said to be particularly effective for dehydration of aqueous solutions of ethanol or isopropanol.

This reference discloses separation of water from alcohols, ethers, ketones, aldehydes, or acids by use of composite membranes. Specifically the composite includes (i) a backing typically about 120 microns in thickness, on which is positioned (ii) a microporous support layer of a polysulfone or a polyacrylonitrile of about 50 microns thickness, on which is positioned (iii) a separating layer of cross-linked polyvinyl alcohol about 2 microns in thickness.

Polyvinyl alcohol may be cross-linked by use of difunctional agents which react with the hydroxyl group of the polyvinyl alcohol. Typical cross-linking agent may include dialdehydes (which yield acetal linkages), diacids or diacid halides (which yield ester linkages), dihalogen compounds or epichlorhydrin (which yield ether linkages) olefinic aldehydes (which yield ether/acetal linkages), boric acid (which yields boric ester linkages), sulfonamidoaldehydes, etc.

U.S. Pat. No. 4,728,429 to Cabasso et al, U.S. Pat. No. 4,067,805 to Chiang et al, U.S. Pat. No. 4,526,948 to Resnick, U.S. Pat. No. 3,750,735 to Chiang et al, and U.S. Pat. No. 4,690,766 to Linder et al provide additional background.

Additional prior art which may be of interest includes:

*Mobility of Spin Probes in Quaternized Poly(4-Vinylpyridine) Membranes,* Makino, Hamada, and Iijima, in Polym.

J. (Toyko), 19 (6), 737–45, 1987.

*Effect of Quaternization on the Pervaporation Rate of Water Through poly(4-Vinylpyridine) Membrane,* Hamaya, and Yamada, in Kobunshi Ronbunshu, 34(7), 545–7, 1977.

*Preparation of Separation Membranes,* Yamamoto, Toi, and Mishima, patent #JP 61/161109 A2, Jul. 21 1986. (Japanese).

*Separation of Some Aqueous Amine Solutions by Pervaporation through Poly(4-Vinylpyridine) Membrane* Yamada and Hamaya, in Kobunshi Ronbunshu, 39(6), 407–14, 1982.

*Complex Formation of Crosslinked Poly(4-Vinvlpyridine) Resins with Copper (II),* by Nishide, Deguchi, and Tsuchida, in Bulletin of the Chemical Society of Japan, Vol. 49(12), 3498–3501 (1976).

It is an object of this invention to provide a novel process for separation of water from organic oxygenates such as isopropyl alcohol. Other objects will be apparent to those skilled in the art.

STATEMENT OF THE INVENTION

In accordance with certain of its aspects, this invention is directed to the method of concentrating a charge aqueous solution of an organic oxygenate which comprises.

maintaining a non-porous separating layer of a poly(vinyl pyridine) a portion of the nitrogen groups of which have been quaternized and which has been cross-linked with a polyhalide;

maintaining a pressure drop across said non-porous separating layer of poly(vinyl pyridine);

passing a charge aqueous solution of an organic oxygenate into contact with the high pressure side of said non-porous separating layer of poly(vinyl pyridine) whereby at least a portion of said water in said charge aqueous solution and a lesser portion of organic oxygenate in said charge aqueous solution pass by pervaporation through said non-porous separating layer as a lean mixture containing more water and less organic oxygenate than are present in said charge aqueous solution and said charge aqueous solution is converted to a rich liquid containing less water and more organic oxygenate than are present in said charge aqueous solution;

recovering as permeate from the low pressure side of said non-porous separating layer, said lean mixture containing more water and less organic oxygenate than are present in said charge aqueous solution, said lean mixture being recovered in vapor phase at a pressure below the vapor pressure thereof; and recovering as retentate from the high pressure side of said non-porous separating layer said rich liquid containing a lower water content and a higher organic oxygenate content than are present in said charge aqueous solution.

DESCRIPTION OF THE INVENTION

The composite structure of this invention includes a multi-layer assembly which in the preferred embodiment preferably includes a porous carrier layer which provides mechanical strength and support to the assembly.

THE CARRIER LAYER

This carrier layer, when used, is characterized by its high degree of porosity and mechanical strength. It may be fibrous or non-fibrous, woven or non-woven. In the preferred embodiment, the carrier layer may be a porous, flexible, non-woven or woven fibrous polyester.

One typical non-woven polyester carrier layer may be formulated of non-woven, thermally-bonded strands and characterized by a fabric weight of 80±8 grams per square yard, a thickness of 4.2±0.5 mils, a tensile strength (in the machine direction) of 31 psi and (in cross direction) of 10 psi, and a Frazier air permeability of 6 cuft/min/sq. ft. @ 0.5 inches of water.

THE POROUS SUPPORT LAYER

The porous support layer of this invention is preferably formed of a sheet or membrane of polyvinylidene fluoride, a teflon polyfluoroethylene polymer, or more preferably of polyacrylonitrile. Typically the support layer may be of thickness of 40–80 microns, say 50 microns and of molecular weight $\bar{M}_n$ of 5,000–100,000, preferably 20,000–60,000 say 40,000. The polyacrylonitrile is preferably characterized by a pore size of less than about 500 A and typically about 200 A. This corresponds to a molecular weight cut-off of less than about 100,000, typically about 20,000.

A preferred porous support layer may be the Daicel DUY-L polyacrylonitrile of 40,000 molecular weight cutoff.

Typically the support layer may be characterized by a molecular weight $M_n$ of 100,000, a $T_m$ of 319° C., a $T_g$ of 85° C., a decomposition temperature of 250° C. a tensile strength at yield of 250–568 MPa, a Linear Thermal Expansion Coefficient of $1.6 \, K^{-1}$ (above $T_g$) and of $1.0 \, K^{-1}$ (below $T_g$), and Water Absorption (at 21° C. and 65% relative humidity) of 1–2.5%. ($T_m$ is the melting point and $T_g$ is the glass transition temperature).

THE SEPARATING LAYER

The separating layer or membrane which permits attainment of separation in accordance with this invention includes a non-porous film of cross-linked poly(vinyl pyridine) of thickness of about 1–10 microns, preferably 1–5 microns, say 3 microns. This layer is formed (preferably by casting) from a poly(vinyl pyridine). Although poly(2-vinyl pyridine) may be employed, the preferred separating layer is prepared from poly(4-vinyl pyridine)—typically the Reilline 4200 brand (of Reilly Tar and Chemical Co) of poly(4-vinyl pyridine) in a 10 w % solution in a suitable alcohol solvent such as methanol.

The membrane may be formed by mixing 0.5–2 parts, say 1 part of the 10%–30%, say 10w % solution of poly(4-vinyl pyridine) in methanol with 1 part methanol, and 0.1–0.8 parts, say 0.52 parts of aliphatic polyhalide cross-linking agent and casting the mixture on a support.

It is a feature of this invention that the separating layer may be a homopolymer or a copolymer of 2-vinyl pyridine or more preferably 4-vinyl pyridine. When copolymers are employed, the co-monomer may be an ethlenically unsaturated monomer, typically vinyl chloride, ethylene, vinyl alcohol, styrene, vinyl acetate, ethylene oxide, or acetonitrile etc. In the preferred embodiment, the separating layer is a homopolymer of 4-vinyl pyridine of molecular weight $\bar{M}_n$ of 10,000–500,000, preferably 100,000–300,000, say about 200,000.

In accordance with practice of the process of this invention, the poly(vinyl pyridine)-containing polymer, in membrane form, may be treated with a monohalo quaternizing agent. The polymer membrane, prior to quaternization may typically contain (per 1000 units of molecular weight $\bar{M}_n$) about 9.5 quaternizable nitrogen atoms. During quaternization, less than all of these quaternizable nitrogen atoms, preferably 1%–90%, say 50% may be reacted with the quaternizing agent and converted to quaternary form.

The monohalo quaternizing agent is preferably a chloro- or bromo- agent. Although it may be an aryl, alkaryl, aralkyl, or cycloalkyl chloride or bromide, it is more preferably an alkyl bromide i.e. a monobromo alkane.

The monohalo quaternizing agent may be an oxygenated compound typified by a halo alcohol (including a monohalo glycol) or a monohalo lactone.

Illustrative monohalo quaternizing agents may include:

TABLE

| Alkylhalides | 1-bromobutane |
| --- | --- |
| | 1-bromopropane |
| | 2-bromopropane |
| | methyl bromide |
| | methyl chloride |
| | 1-chlorobutane |
| Cycloalkyl halide | cyclohexyl bromide |
| | cyclohexyl chloride |
| Aralkyl halides | benzyl chloride |
| | benzyl bromide |
| Alkaryl halides | 2-chloro toluene |
| | 3-bromo toluene |
| | 4-bromo toluene |
| Haloalcohols | 1-bromo-propanol-2 |
| | chloroethanol |
| | 3-bromo-propanol-1 |
| | 4-bromo-butanol-1 |
| | 3-bromo-butanol-1 |
| | p-bromo-benzyl alcohol |
| | 2-bromo-butane diol-1,4 |
| Halolactones | 2-bromo butyrolactone |
| | 3-chloro butyrolactone |
| | 1-bromo-gamma-butyrolactone |
| Halonitriles | bromo acetonitrile |
| | 4-bromo butyronitrile |

The preferred monohalo quaternizing agent may be bromo- compounds including 2-bromo butyrolactone, bromoacetonitrile, 3-bromo-propanol-1, and most preferably 1-bromo-n-butane (i.e., n-butyl bromide).

It is possible to quaternize the membrane first and to cross-link subsequently as long as the quaternized product does not precipitate out. Otherwise it is preferred that they be effected simultanously i.e. by forming the poly(vinyl pyridine) membrane in the presence of both (i) the monohalo- quaternizing agent and (ii) the polyhalo-cross-linking agent.

Typically the cross-linking agents may contain an aliphatic moiety, preferably containing 2–12 carbon atoms, typically 3–6 carbon atoms, say 4 carbon atoms. Although the cross-linking agent may be a polyhalide, it typically contains 2–5 halogen atoms, most preferably 2. The halogen is preferably bromine. Chlorine or iodine may be used. The halides may preferably be alpha, omega dihalides of linear straight chain aliphatic hydrocarbon. Typical cross-linking agents may be as tabulated infra, the first listed being preferred:

TABLE

| 1,4-dibromo-n-butane | (DBB) |
| --- | --- |
| 1,5-dibromo-n-pentane | (DBP) |
| 1,3-dibromo propane | |
| 1,6-dibromo hexane | |
| 1,8-dibromo octane | |
| 1,4-dichloro-n-butane | |
| 1,4-dibromo-butanediol-2,3 | |

In situ cross-linking may be carried out by casting onto the preferred polyacrylonitrile support the poly(4-vinyl pyridine) typically in the solution in methanol to which is added the cross-linking agent (typically 1,4-dibromobutane) in mole ratio of cross-linking agent to polymer of 0.2–2, say about 1.13.

It may be possible in one embodiment to cross-link the poly(4-vinyl pyridine) separating layer in one step by casting the solution of poly(4-vinyl pyridine) and polyhalide, followed by heat curing the cast membrane at 100° C.–200° C., say 125° C. for 1–30 minutes, say 2 minutes.

In another embodiment, it may be possible to apply to the porous support layer, a solution of poly(4-vinyl pyridine). This may be dried at 40° C.–80° C., say 50° C. for 2–10 minutes, say 4 minutes to form a film. There may then be added onto the surface of this uncross-linked film a solution in methanol containing polyhalide and 2–7w %, say 3.5w % of poly (4-vinyl pyridine).

The composite membrane, whether prepared by the one-step or the two-step process may then be cured in an oven at 100° C.–200° C., say 125° C. for 1–30 minutes, say 2 minutes to yield a film having a thickness of 1–10 microns, say 4 microns.

In one preferred embodiment, the membrane may be prepared by casting a solution containing 5–20, say 7.95 parts of poly(vinyl pyridine) in 20–40, say 31.74 parts of methanol and 20–40 parts, say 31.74 parts of monohaloalkane quaternizing agent and 10–20 parts, say 12.70 parts of dihaloalkane and 10– 30 parts, say 15.87 parts of n-butanol onto the surface of the polyacrylonitrile support.

THE COMPOSITE MEMBRANE

It is a feature of this invention that the composite membrane of this invention may comprise (i) an optional carrier layer, characterized by porosity and mechanical strength, for supporting a porous support layer and a separating layer, (ii) a porous support layer of preferably polyacrylonitrile of molecular weight $\bar{M}_n$ of 5,000–100,000, of thickness of 10–80 microns, and of molecular weight cut off of 25,000–100,000 and (iii) as a non-porous separating layer poly(vinyl pyridine) of molecular weight $\bar{M}_v$ of 10,000–500,000 which has been quaternized with a monohalo quaternizing agent and cross-linked with an aliphatic polyhalide.

The composite membranes of this invention may be utilized in various configurations. It is, for example, possible to utilize the composite in a plate-and-frame configuration in which separating layers may be mounted on the porous support layer with the carrier layer.

It is possible to utilize a spiral mound module which includes a non-porous separating layer membrane mounted on a porous support layer and a carrier layer, the assembly being typically folded and bonded or sealed along all the edges but an open edge—to form a bag-like unit which preferably has the separating layer on the outside. A cloth spacer, serving as the permeate or discharge channel is placed within the bag-like unit. The discharge channel projects from the open end of the unit.

There is then placed on one face of the bag-like unit, adjacent to the separating layer, and coterminous therewith, a feed channel sheet—typically formed of a plastic net.

The so-formed assembly is wrapped around a preferably cylindrical conduit which bears a plurality of perforations in the wall—preferably in a linear array which is as long as the width of the bag-like unit. The projecting portion of the discharge channel of the bag-like unit is placed over the performations of the conduit; and the bag-like unit is wrapped around the conduit to form a spiral wound configuration.

It will be apparent that, although only one feed channel is present, the single feed channel in the wound assembly will be adjacent to two faces of the membrane layer. The spiral wound configuration may be formed by wrapping the assembly around the conduit a plurality of times to form a readily handleable unit. The unit is fitted within a shell(in manner comparable to a shell-and-tube heat exchanger) provided with an inlet at one end and an outlet at the other. A baffle-like seal between the inner surface of the shell and the outer surface of the spiral-wound input prevents fluid from bypassing the operative membrane system and insures that fluid enters the system principally at one end. The permeate passes from the feed channel, into contact with the separating layer and thence therethrough, into the permeate channel and thence therealong to and through the perforations in the conduit through which it is withdrawn as net permeate.

In use of the spiral wound membrane, charge liquid is permitted to pass through the plastic net which serves as a feed channel and thence into contact with the non-porous separating membranes. The liquid which does not pass through the membranes is withdrawn as retentate. The liquid or vapor which permeates the membrane passes into the volume occupied by the permeate spacer and through this permeate channel to the perforations in the cylindrical conduit through which it is withdrawn from the system. In this embodiment, it will be apparent that the system may not include a carrier layer.

In another embodiment, it is possible to utilize the system of this invention as a tubular or hollow fibre. In this embodiment, the porous support layer of e.g. polyacrylonitrile may be extruded as a fine tube with a wall thickness of typically 0.001–0.1mm. The extruded tubes are passed through a bath of poly(vinyl pyridine) which is quaternized and cross-linked and cured in situ. A bundle of these tubes is secured (with an epoxy adhesive) at each end in a header; and the fibres are cut so that they are flush with the ends of the header. This tube bundle is mounted within a shell in a typical shell-and-tube assembly.

In operation, the charge liquid is admitted to the tube side and passes through the inside of the tubes and exits as retentate. During passage through the tubes, permeate passes through the non-porous separating layer and permeate is collected in the shell side.

In this embodiment, it will be apparent that the system may not normally include a carrier layer. In still another embodiment, the porous support layer may be omitted; and the separating layer is extruded and thereafter crosslinked and cured in situ prior to mounting in the headers.

PERVAPORATION

It is a feature of the non-porous separating layer that it is found to be particularly effective when used in a pervaporation process. In pervaporation, a charge liquid containing a more permeable and a less permeable component is maintained in contact with a non-porous separating layer; and a pressure drop is maintained across that layer. The charge liquid dissolves into the membrane and diffuses therethrough. The permeate which passes through the membrane and exits as a vapor may be recovered by condensing at low temperature or alternatively may be swept away by use of a moving stream of gas. Preferably, the permeate side of the membrane is maintained at a low pressure, typically 5 mm. Hg.

For general background on pervaporation, note U.S. Pat. No. 4,277,344; U.S. Pat. No. 4,039,440; U.S. Pat. No. 3,926,798; U.S. Pat. No. 3,950,247; U.S. Pat. No. 4,035,291; etc.

It is a feature of the process of this invention that the novel membrane may be particularly useful in pervaporation processes for dewatering aqueous mixtures of organic oxygenates. It may be possible to utilize the process of this invention to remove water from immiscible mixtures therewith as in the case of ethyl acetate (solubility in water at 15° C. of 8.5 parts per 100 parts of water). It will be apparent to those skilled in the art that it may be desirable to separate large quantities of water from partially miscible systems as by decantation prior to utilizing the process of the invention to remove the last traces of water.

The advantages of the instant invention are more apparent when the charge liquid is a single phase homogeneous aqueous solution as is the case for example with isopropanol. The system may also find use in the case of slightly soluble liquids wherein two phases are present (i) water-oxygenate first phase and, as a second phase (ii) either water or oxygenate. Clearly those charge liquids which contain only a small portion of an immiscible second liquid phase may benefit most from the process of this invention. It is also a feature of this invention that it may be particularly useful to separate azeotropes such as isopropanol-water.

The charge organic oxygenates which may be treated by the process of this invention may include alcohols, glycols, weak acids, ethers, esters, ketones, aldehydes, etc. It will be apparent to those skilled in the art that the charge organic oxygenates used should be inert with respect to the separating membrane. Clearly a system wherein the membrane is attacked by the components of the charge liquid will not yield significant separation for any reasonable period of time. Best results may be achieved when treating alcohols (such as isopropanol) or glycols (such as ethylene glycol). Results achieved with acids are generally less satisfactory.

Illustrative alcohols may include ethanol, propanol, i-propanol, n-butanol, i-butanol, t-butanol, amyl alcohols, hexyl alcohols, etc.

Illustrative glycols may include ethylene glycol, propylene glycols, butylene glycol or glycol ethers such as diethylene glycol, triethylene glycol, or triols, including glycerine; etc.

Illustrative chlorinated hydrocarbons may include dichloroethane, methylene dichloride, etc.

Illustrative weak acids may include hexanoic acid, octanoic etc. (When acids are present, preferably the pH of the charge liquid should be above about 4. Typical acids which may be treated by the process of this invention include those having a pKa≧ca4.8.

Illustrative esters may include ethyl acetate, methyl acetate, butyl acetate, methyl benzoate, ethylene glycol mono acetate, propylene glycol monostearate, etc.

Illustrative ethers may include tetrahydroforan, diethyl ether, diisopropyl ether, etc.

Illustrative ketones may include acetone, methyl ethyl ketone, acetophenone, etc.

Illustrative aldehydes may include formaldehyde, acetaldehyde, propionaldehyde, etc.

It is believed that the advantages of this invention are most apparent where the organic oxygenate is a liquid which is infinitely miscible with water—typified by isopropyl alcohol or ethylene glycol.

A typical charge may be an aqueous solution containing

70%–95%, say 85w % isopropanol

In practice of the pervaporation process of this invention, the charge aqueous organic oxygenate solution typically at 40° C.–120° C., say 80° C. may be passed into contact with the non-porous separating layer of the membrane of this invention. A pressure drop of about one atmosphere is commonly maintained across the membrane. Typically, the feed or charge side of the membrane is at about atmospheric pressure and the permeate or discharge side of the membrane is at a pressure of about 2–50 preferably 5–20, say 10 mm. Hg.

The permeate which passes through the membrane includes water and a small proportion of the organic oxygenate from the charge liquid. Typically, the permeate contains 80–99.5, say 98w % water. Permeate is recovered in vapor phase.

Performance is judged by the ability of a membrane system to give a permeate containing decreased content of organic oxygenate (from a charge containing a higher content of organic oxygenate and water) with a good flux (kilograms-/meter-$^2$-/hour (kmh)) at a predetermined feed temperature and with a vacuum on the permeate side and a condenser (cooled by liquid nitrogen). Compositions falling outside the scope of this invention may be characterized by unsatisfactory separation or unsatisfactory productivity (flux) or both.

Pervaporation may typically be carried out at a flux of 0.2–3, say 1.2 gallons per square foot per day which corresponds to 0.3–5, say 2 kilograms per square meter per hour (kmh). Typically the units may show separation (measured in terms of w % oxygenate in the permeate during pervaporation of an aqueous solution of organic oxygenate through a poly(4-vinyl pyridine) separating layer) as high as 98%.

Practice of the process of this invention will be apparent to those skilled in the art from inspection of the following examples wherein, as elsewhere in this specification, all parts are parts by weight unless otherwise stated. An asterisk indicates a control example.

DESCRIPTION OF SPECIFIC EMBODIMENTS

EXAMPLE 1

In this example, which represents the best mode presently known of carrying out the process of this invention, the selective separating layer is mounted on the porous support layer of a commercially available (under the trademark DUY-L, from Daicel Corp) composite containing a non-woven polyester backing as carrier layer, bearing as porous support layer, a microporous polyacrylonitrile layer of molecular weight cut-off of 40,000.

The separating layer is formed from a 20w % solution in methanol of 2.5 parts of poly(4-vinyl pyridine), $\bar{M}_v$ of about 200,000, available under the trademark Reilline 4200 from Reilly Tar and Chemical Co., to which has been added 2 parts of n-butyl bromide. The mixture is stirred at room temperature of ca 25° C. for 16–24 hours. 0.8 parts of 1,6-dibromo-n-hexane in 1 part of n-butanol are then added.

This mixture is then applied to the porous support acrylonitrile layer which has been etched with sulfuric acid at a pH<1. The applied layer (thickness of 2 mils) is then cured at 125° C. for 2 minutes.

This membrane assembly is evaluated in a pervaporation cell to which the charge is admitted at 70° C. Permeate pressure is 2 torr at liquid nitrogen temperature.

In this preferred embodiment, the charge solution is an 85w % solution of ethylene glycol in water. The permeate condenser contains an aqueous solution containing only about 1–2w % glycol and (Selectivity) 97–98w % water Flux is 0.4–0.9 kmh.

EXAMPLE 2

In this Example, the procedure of Example 1 is followed except for the following:

(i) the quaternizing agent (replacing an equal part by weight of n-butyl bromide) is 1-bromo-gamma-butyrolactone; and (ii) the porous polyacrylonitrile is not treated with acid but rather with oxygen-plasma (25 mm torr, 30 sec, at a radio frequency of 13.5 MHz) and the resulting wet membrane is cured at 125° C. for 2 minutes.

Evaluation of this assembly in manner comparable to Example 1 yields a permeate solution containing 8w % of glycol and 92w % water. Flux is 0.4 kmh.

EXAMPLE 3

In this Example, the procedure of Example 1 is followed except for the following:

(i) the amount of n-butyl bromide quaternizing agent is 1 part;

(ii) the cross-linking agent is 0.8 parts of 1,4-dibromo-2, 3-butanediol in 2 parts of 1-hexanol Evaluation indicates a permeate solution containing 4w % glycol and 96w % water. Flux is 0.7 kmh.

EXAMPLE 4*

In this control Example, the procedure of Example 1 is followed except that no n-butyl bromide quaternizing agent is employed.

Evaluation indicates a permeate solution containing 30w % glycol and 70w % water. Flux is 0.4 kmh.

EXAMPLE 5*

In this control Example, the procedure of Example 2 is followed except that no 1-bromo-gamma-butyrolactone quaternizing agent is employed.

Evaluation indicates a permeate solution containing 30w % glycol and 70w % water. Flux is 0.4 kmh.

EXAMPLE 6

In this Example, there is charged an 85w % solution of isopropanol in water at 70° C. to the membrane of Example I. No acid etching agent or oxygen plasma is applied to the support. The selectivity is 93% and the Flux is 4.0 kmh.

EXAMPLE 7*

In this control Example, the membrane and charge is identical to that of Example 6 except that no quaternizing agent is employed. Selectivity is 98% but Flux is only 2.9.

Results comparable to those of Example 1 may be attained if the charge aqueous liquid contains:

TABLE

| EXAMPLE | CHARGE |
| --- | --- |
| 8 | 90% diethylene glycol |
| 9 | 80% n-propanol |

Although this invention has been illustrated by reference to specific embodiments, it will be apparent to those skilled in the art that various charges and modifications may be made which clearly fall within the scope of the invention.

What is claimed:

1. The method of concentrating a charge aqueous solution of an organic oxygenate which comprises.

maintaining a non-porous separating layer of a poly(vinyl pyridine) polymer a portion of the nitrogen groups of which have been quaternized and which has been cross-linked with a polyhalide;

maintaining a pressure drop across said non-porous separating layer of poly(vinyl pyridine);

passing a charge aqueous solution of an organic oxygenate into contact with the high pressure side of said non-porous separating layer of poly(vinyl pyridine) whereby at least a portion of said water in said charge aqueous solution and a lesser portion of organic oxygenate in said charge aqueous solution pass by pervaporation through said non-porous separating layer as a lean mixture containing more water and less organic oxygenate than are present in said charge aqueous solution and said charge aqueous solution is converted to a rich liquid containing less water and more organic oxygenate than are present in said charge aqueous solution;

recovering as permeate from the low pressure side of said non-porous separating layer, said lean mixture containing more water and less organic oxygenate than are present in said charge aqueous solution, said lean mixture being recovered in vapor phase at a pressure below the vapor pressure thereof; and recovering as retentate from the high pressure side of said non-porous separating layer said rich liquid containing a lower water content and a higher organic oxygenate content than are present in said charge aqueous solution.

2. The method of claim 1 wherein said quaternization is effected with a mono-haloquaternizing agent selected from the group consisting of alkyl halide, cycloalkyl halide, aralkyl halide, alkaryl halide, halo acohol, halo lactone, and halo nitrile.

3. The method of claim 1 wherein said quaternization is effected with 1-bromo-gamma-butyrolactone 1-bromo-n-butane.

3-bromo-propanol-1 bromoacrylonitrile or 2-bromobutyrolactone

4. The method of claim 1 whrein said cross-linking and said quaternization are effected simultaneously.

5. The method of claim 1 wherein said cross-linking is effected with an alpha, omega dihalide of a linear straight chain aliphatic hydrocarbon.

6. The method of claim 1 wherein said organic oxygenate is an alcohol, glycol, weak acid, ether, ester, ketone, or aldehyde.

7. The method of claim 1 wherein said organic oxygenate is an aliphatic alcohol.

8. The method of concentrating a charge aqueous solution of ethylene glycol maintaining a non-porous separating layer of a poly(4-vinyl pyridine) polymer a portion of the nitrogen groups of which have been quaternized with n-butyl bromide and which has been cross-linked with 1,6-dibromo-n-hexane;

maintaining a pressure drop across said non-porous separating layer of poly(4-vinyl pyridine);

passing a charge aqueous solution of an organic oxygenate into contact with the high pressure side of said non-porous separating layer of poly(4-vinyl pyridine) whereby at least a portion of said water in said charge aqueous solution and a lesser portion of ethylene glycol in said charge aqueous solution pass by pervaporation through said non-porous separating layer as a lean mixture containing more water and less ethylene glycol than are present in said charge aqueous solution and said charge aqueous solution is converted to a rich liquid containing less water and more ethylene glycol than are present in said charge aqueous solution;

recovering as permeate from the low pressure side of said non-porous separating layer, said lean mixture containing more water and less ethylene glycol than are present in said charge aqueous solution, said lean mixture being recovered in vapor phase at a pressure below the vapor pressure thereof; and recovering as retentate from the high pressure side of said non-porous separating layer said rich liquid containing a lower water content and a higher ethylene glycol content than are present in said charge aqueous solution.

9. A membrane comprising a non-porous separating layer of a poly(vinyl pyridine) polymer a portion of the nitrogen groups of which have been quaternized and which has been crosslinked with a polyhalide.

10. A membrane as claimed in claim 9 wherein said quaternization have been effected with a monohalo quaternizing ageng selected from the group consisting of alkyl halide, cycloalkyl halide, aralkyl halide, alkaryl halide, haloalcohol, halolactone, and halonitrile.

11. A membrane as claimed in claim 9 wherein said quaternization has been effected with 1-bromo-gamma-butyrolactone 1-bromo-n-butane 3-bromo-propanol-1 bromoacrylonitrile or 2-bromobutylolactone 12. A membrane as claimed in claim 9 wherein said cross-linking and said quaternization are effected simultaneously.

13. A membrane as claimed in claim 9 wherein said cross-linking is effected with an alpha, omega dihalide of a linear straight chain aliphatic hydrocarbon.

14. A membrane as claimed in claim 9 wherein said organic oxygenate is an alcohol, glycol, weak acid, ether, ester, ketone, or aldehyde.

15. A membrane comprising a non-porous separating layer of poly(4-vinyl pyridine) polymer a portion of the nitrogen groups of which have been quaternized with n-butyl bromide and which has been cross-linked with 1,6-dibromo-n-hexane.

* * * * *